United States Patent
Miller et al.

(10) Patent No.: US 7,118,597 B2
(45) Date of Patent: Oct. 10, 2006

(54) ACCOMMODATING INTRAOCULAR LENS

(76) Inventors: David Miller, 9 Francis St., Brookline, MA (US) 02446; Ernesto Blanco, 36 Sandrick Rd., Belmont, MA (US) 02178

( * ) Notice: Subject to any disclaimer, the term of this patent is extended or adjusted under 35 U.S.C. 154(b) by 0 days.

(21) Appl. No.: 10/964,863

(22) Filed: Oct. 14, 2004

(65) Prior Publication Data

US 2005/0113914 A1     May 26, 2005

Related U.S. Application Data

(63) Continuation-in-part of application No. 10/738,271, filed on Dec. 17, 2003, which is a continuation-in-part of application No. PCT/US02/19534, filed on Jun. 21, 2002.

(60) Provisional application No. 60/299,757, filed on Jun. 22, 2001.

(51) Int. Cl.
    *A61F 2/14*     (2006.01)
(52) U.S. Cl. .................................... 623/6.37
(58) Field of Classification Search ................ 623/4.1, 623/5.14, 5.15, 6.11, 6.14, 6.22, 6.27, 6.34, 623/6.37–6.4, 6.52
    See application file for complete search history.

(56) References Cited

U.S. PATENT DOCUMENTS 6,494,911 B1 * 12/2002 Cumming ................... 623/6.37
6,749,634 B1 *  6/2004 Hanna ......................... 623/6.37
6,846,326 B1 *  1/2005 Zadno-Azizi et al. ....... 623/6.34

FOREIGN PATENT DOCUMENTS

JP         2126847      *  5/1990

OTHER PUBLICATIONS

Translation of JP 2126847.*

* cited by examiner

*Primary Examiner*—Corrine McDermott
*Assistant Examiner*—William H Matthews
(74) *Attorney, Agent, or Firm*—Robert F. I. Conte; Barnes & Thornburg LLP

(57) ABSTRACT

An intraocular lens arrangement having positive or negative lens with a frame that extends from the lens to provide diametrically opposed upper and lower frame sections. A first lens linkage has its first end attached to the upper frame section with at least two points of contact with the upper frame section. A second lens linkage has its first end attached to the lower frame section with at least two points of contact with the lower frame section. A second end of said first lens linkage and a second end of the second lens linkage are attached to a sulcus or zonule member to provide relatively large movement of the lens with a small movement of the ciliary muscle during accomodation response of the eye, and wherein the movements during the accommodation response are along the optical axis of the eye and are controlled in order to improve the image on the retina of objects viewed by the eye over a wide range of distances. The lens is preferably a positive lens with the appropriate frame. The haptics that connect the frame to the sulcus member is at least two pairs of haptics or alternatively a pair of single curved haptics that each have a sulcus connecting member. The intraocular lens cand contain a positive lens as note above along with a negative lens.

2 Claims, 3 Drawing Sheets

ACCOMMODATING INTRAOCULAR LENS

This is a continuation-in-part of our U.S. application Ser. No. 10/738,271 filed Dec. 17, 2003 which is based on PCT application PCT/US02/19534 filed Jun. 21, 2002 which claims priority of our U.S. provisional application 60/299,757 filed Jun. 22, 2001.

FIELD OF THE INVENTION

This invention relates to intraocular lenses and more particularly to intraocular lenses that have a frame extending from the lens and haptics connected to the frame on at least two upper and two lower points on the frame and connected to a sulcus or zonule member to move the lens along an optical axis in response to the movement of the eye ciliary sulcus or zonules and which may be implanted in the eye.

BACKGROUND

The lens within the human eye has the capability of changing shape and thereby focus so that objects both far and near can be registered sharply on the retina. This ability to change focus is known as accommodation. With age, the lens gradually loses its range of accommodation. The human lens not only loses accommodative range with aging, but also transparency. When the lens loses a significant amount of transparency (thus producing a blurry image on the retina), it is said that the lens is cataractous or has become a cataract. Treatment for a cataract requires the surgical removal of the cataract and the placing of a man made synthetic lens (intraocular lens or IOL) in the eye. The earlier IOL's had a fixed focus and thus had no accommodative function.

However, in time a number of IOL's were designed in multifocal form. Different zones of a multifocal IOL have different dioptric powers. With such multifocal IOL's, light from objects, only within a specific range of viewing distances, passing through a particular zone will form sharply focused images on the retina. On the other hand, if an object is outside this range, its image formed by the zone under consideration will be blurry. Multifocal IOL's typically have two or more zones, each designed for a specific viewing distance. A consequence of this design approach is that the imagery of multifocal IOL's is never very sharp. The success of multifocal IOL's depends on the visual processing system of the patient's eye and brain that tends to pay attention to the light most sharply focused on the retina, and tends to ignore the light formed diffusely on the retina.

These were followed by IOL's that could move back and forth via ciliary muscle contraction and thus focus objects from different distances onto the retina. However, these IOL's have limited range of movement and thus a limited accommodative range.

Another form of IOL is made of an elastomer filled flexible balloon which is placed within the emptied lens capsule and alters lens shape under the influence of the ciliary muscle contraction.

Another accommodative IOL design is comprised of two positive lens elements (i.e. two plano-convex lenses) connected by two flexible hinges. The lens components are spread or come together in response to ciliary muscle contraction.

In our invention, we have an intraocular lens that preferably has an integral frame that enclosed at least 25% of the outer circumference of the lens i.e. 90° out of 360° of a circular lens.

Also we have an accommodative IOL that can be used alone or can be a combination of a positive lens (i.e. lens is thicker at center than at edge), and a negative lens (i.e. lens is thinner at center than at edge). Also, our IOL can alter dioptric power if placed in either of two intra ocular locations: a) within the capsular bag, or b) placed within the ciliary sulcus. In both locations, the contraction of the ciliary muscle alters the position of the lens.

SUMMARY OF INVENTION

The present invention provides:

1. An intraocular lens having a lens, a frame extending from the lens, a lens linkage attached to the frame using at least four points of connection (two upper and two lower connections) on the frame and attached to a sulcus or zonule member to provide relatively large movement of the lens with a small movement of the ciliary muscle.

2. An intraocular lens having a lens, a first linkage having a first end connected to at least two contact points on the lower portion of the lens frame and a second end connected to an upper portion of the ciliary sulcus or zonule member, and a second linkage having its first end connected to at least two contact points on the upper portion of the lens frame and its second end to be connected to a lower portion of the ciliary sulcus or zonule member.

3. Intra ocular lenses as noted in above 1–2 wherein the lens is a positive lens and the intraocular lens is implanted in or outside of the lens capsule or capsular bag.

4. An intraocular lens as noted in above 1–3 wherein the intraocular lens includes the positive lens of above 1–2 and a negative lens.

One embodiment of the present invention is to provide an intra ocular lens having a lens, a frame enclosing at least 25% of the outer circumference of the lens i.e. 90° out of 360° of a circular lens with diametrically opposed upper and lower frame sections. The frame is preferably integral with the lens and the frame has connected thereto linkages hereinafter referred to as haptics that extend from the frame to a ciliary sulcus or zonule member. There are at least two haptics. One haptic has one end connected to a first frame portion with the one end having at least two contact points with the first frame portion. The other haptic has one end connected to a second frame portion with the one end having at least two contact points with the second frame portion. The first frame portion is diametrically opposite the second frame portion.

A second embodiment of the present invention is to provide an eye intra ocular lens that has a negative lens and a positive lens that are axially separated and said intra ocular lens is formed inside the eye as part of an implantation of the negative and positive lenses in an eye or outside of the eye by connecting the negative and positive lenses prior to implantation into the eye such that the positive lens will move relative to the negative lens and the positive lens has the lens frame as described above and hereinafter.

For the purpose of promoting an understanding of the principles of the invention, references will be made to the embodiment illustrated in the drawings. Specific language will also be used to describe the same. It will, nevertheless, be understood that no limitation of the scope of the invention is thereby intended, such alterations and further modifications in the illustrated device, and such further applications of the principles of the invention illustrated herein being contemplated as would normally occur to one skilled in the art to which the invention relates.

DETAILED DESCRIPTION OF INVENTION

Our invention relates to an intraocular lens (IOL), having either a positive lens and/or a negative lens. When two lenses (positive and negative lenses) are to be used in one eye, the positional order of the lenses in the eye can be either with the positive lens more anterior or the reverse, or with the negative lens more anterior or the reverse. Each single or dual lens system may be placed either outside or within the capsular bag. The two lens system may or may not have the two lenses mechanically linked to one another by tabs and strut-like linkages (haptics) attached to the two lenses. During cataract surgery and IOL implantation, the positive and/or negative lenses may be inserted intra ocularly either one at a time (if the components are not mechanically linked to one another), or both at the same time (if the components are mechanically linked to one another). The linkages serve to hold the positive and negative lenses in place, as well as serve to adjust and control the distance separating the two lenses when powered by ciliary muscle contraction. It is the separation between the lenses that accounts for the change in IOL power (i.e. accommodation).

The lenses are located preferably with a common axis which is also common with the optical axis of the eye (coaxial configuration). This coaxial configuration is maintained during the change in separation of the lens elements which causes the eye's accommodative response. The positive-negative lens configuration provides a greater change of dioptric power with change in separation distance than any other configuration such as a positive-positive or a singlet positive configuration.

Our intraocular lens has a linkage that provides axial movement of the lens by connecting the haptics to a lens frame as hereinafter described in detail. Our linkage can be used on either or both the negative or positive lens when a dual lens is used and it is preferably used on the positive lens.

The positive and negative lenses generally will have spherical surfaces; however, since astigmatic and other aspherical-shaped singlet IOL's (both symmetric and asymmetric with respect to their optical axes) now are manufactured for implantation in the eye, the positive and negative lenses may also have these more general surface shapes. Fresnel-type IOL lenses also are used in cataract surgery. These lenses generally have a succession of stepped-annular zones or facets which serve to minimize a Fresnel lens's thickness while maximizing it power. Fresnel-type positive and negative lenses are suitable lens components for use in our invention. Also, diffractive lens configurations are sometimes used (i.e., diffractive lenses or lenses with one surface diffractive and the other surface refractive.

Figure 8:
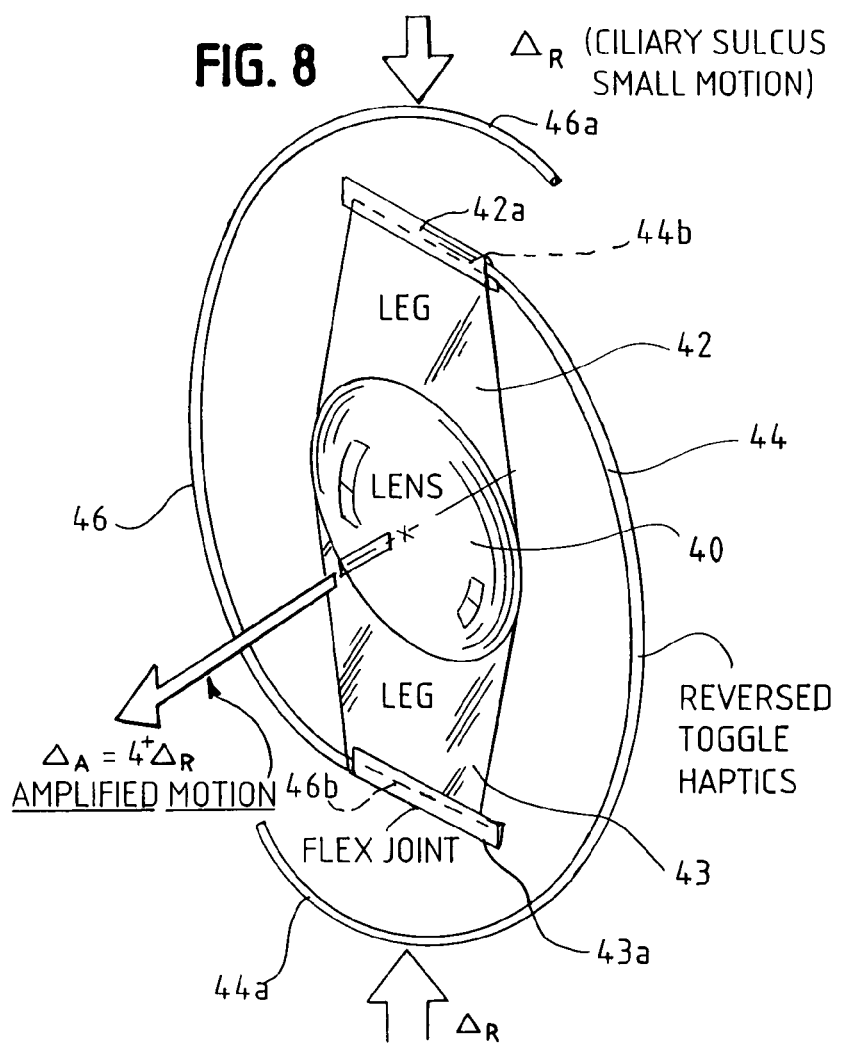
FIG. 8 illustrates a dual lens system according to the present invention.
Figure 9:
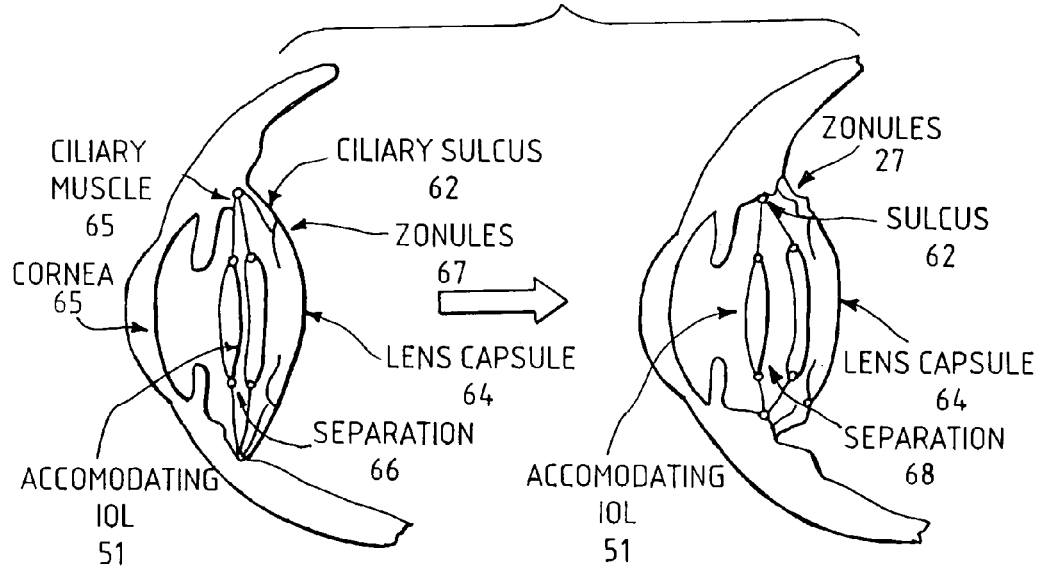
FIG. 9 illustrates the IOL of FIG. 8 connected to the ciliary sulcus.
Figure 10:
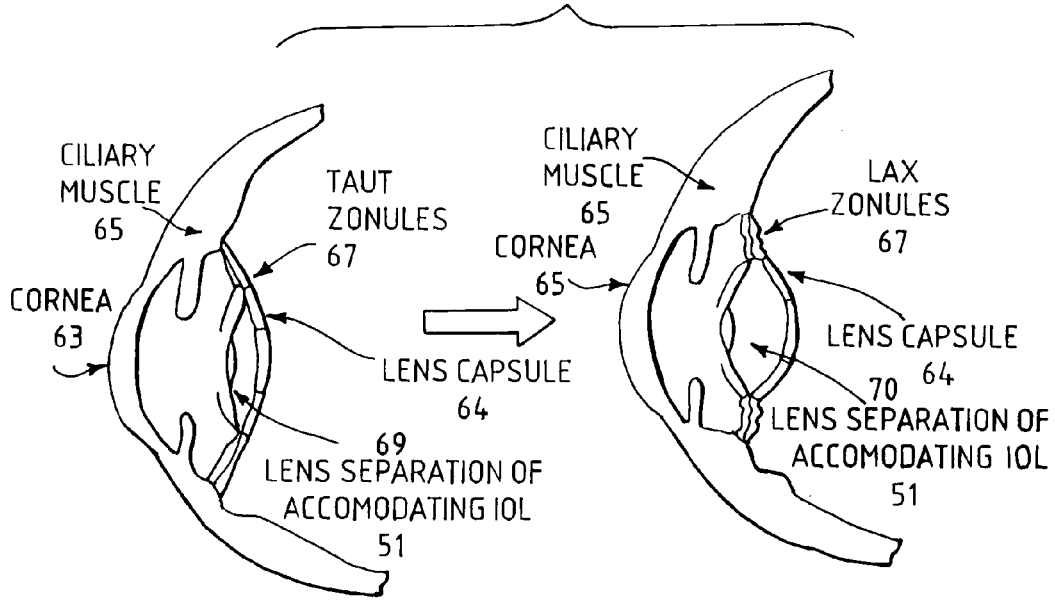
FIG. 10 illustrates the IOL of FIG. 8 within a lens capsule

Generally, a person is not reading and is looking at objects more than two feet away. In that condition, the ciliary muscle is relaxed and the eye is focused on a distant object. When a two lens IOL is used, as shown in FIGS. 8–10, the positive lens and negative lens are brought together with a slight space there between. The spacing is necessary to prevent the two lenses from adhering to each other. Our co pending U.S. Application sets forth the reason why the IOL spacing is larger when the eye's focus changes from viewing a distant object to viewing a nearby object and those are incorporated in this application.

The preferred manner of correcting a patient's vision using a dual lens in one eye is to open the eye's lens capsule or capsule bag, remove the eye lens and first insert the desired positive or negative lens in the lens capsule or capsule bag. Then the other lens is inserted into the lens capsule or capsule bag. The positive lens and negative lenses are connected to each other such that when the ciliary muscle contracts, the two lenses axially separate from each other and when the ciliary muscle relaxes, the two lenses axially move towards each other. In our invention generally, only one of the lenses (preferably the positive lens) moves and the other lens (the negative lens) does not move or moves substantially less and both lenses remain substantially coaxial with each other. One manner of connecting the two lenses to each other would be to connect them both independently to the ciliary muscle and the ciliary muscle zonules. Another method would be to attach the linkages of the positive lens to the linkages of the negative lens. The attachment could be any suitable attachment that would allow the lenses to move away from the each other when the ciliary muscle contracts and towards each other when the ciliary muscle relaxes.

Examples of our IOL having a singlet positive lens is hereinafter described when referring to FIGS. 1–7

Figure 1:
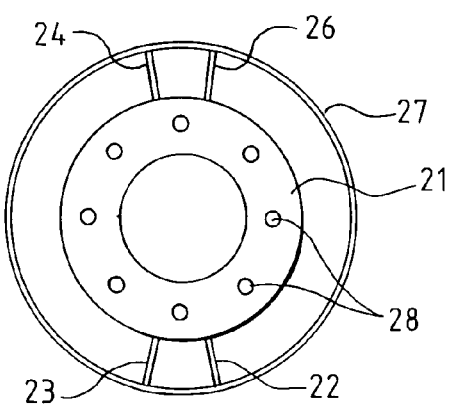
FIG. 1 is a front plane view of an intraocular lens according to the present invention.
Figure 2:
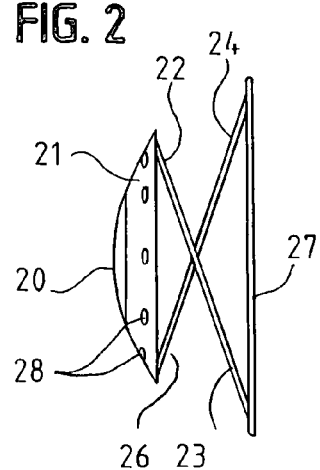
FIG. 2 is a left side view of the lens of FIG. 1.
Figure 3:
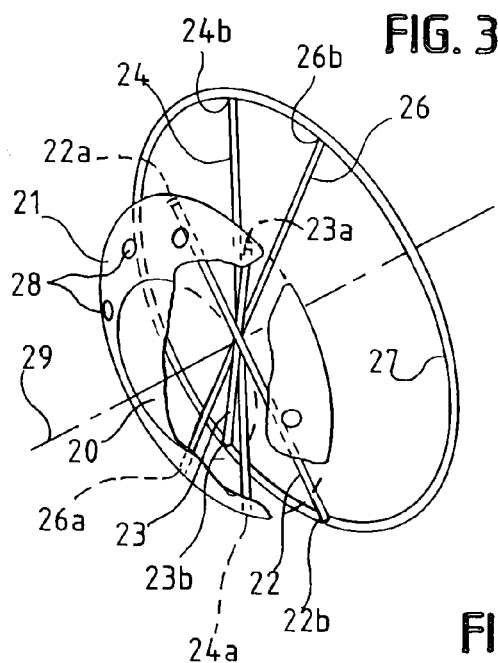
FIG. 3 is a perspective view of the lens of FIG. 1.

FIGS. 1–3 show a positive lens 20 having a circular frame 21 integral therewith and radially extending from the outer circumference of the lens. A pair of upper haptics 22 and 23 have first ends 22a, 23a respectively connected to the upper portion of the frame 21 and the ends are spaced at least 15° apart. A pair of lower haptics 24 and 26 have first ends 24a, 26a respectively connected to the lower portion of the frame 21 and the ends 24a and 26a are spaced at least 15° apart. A sulcus or zonule connecting ring 27 is axially spaced from the lens 20 and is sized to be connected to the ciliary sulcus or to be placed in the eye capsule and connected to to the ciliary muscle through the respective zonules.

The point of connection of the haptic ends 22a, 23a, 24a and 26a all lie in the same plane which is vertical to the lens axis 29. The point of connection for 22a is diagonal to the point of connection for 24a. The point of connection for 23a is diagonal to the point of connection for 26a.

The frame 21 preferably has a plurality of holes 28 therein to reduce the weight of the IOL and also to permit flexibility of the IOL. The lens 20 shown is a positive lens but as stated above if it is desired this may be a negative lens. The circular frame 21 preferably has a convex shape. The haptics 22, 23, 24, and 26 are considered reverse toggle haptics.

The second end 22b of haptic 22 and the second end 23b of haptic 23 are connected to the lower portion of the ring 27 on opposite sides of the optical axis 29 than their respective upper ends 22a and 23a. The second end 24b of haptic 24 and the second end 26b of haptic 26 are connected to the upper portion of the ring 27 on opposite sides of the optical axis 29 than their respective upper ends 24a and 26a. As hereinafter set forth, when the ciliary muscle causes the ring to compress, the lens 20 moves away from the ring 27.

Figure 4:
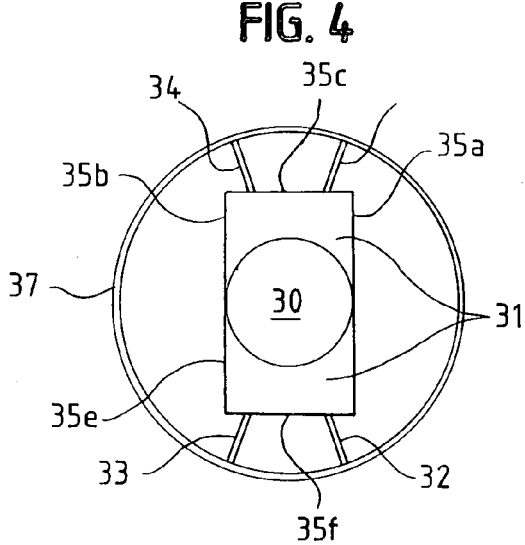
FIG. 4 is a front plane view of another intraocular lens according to the present invention.
Figure 5:
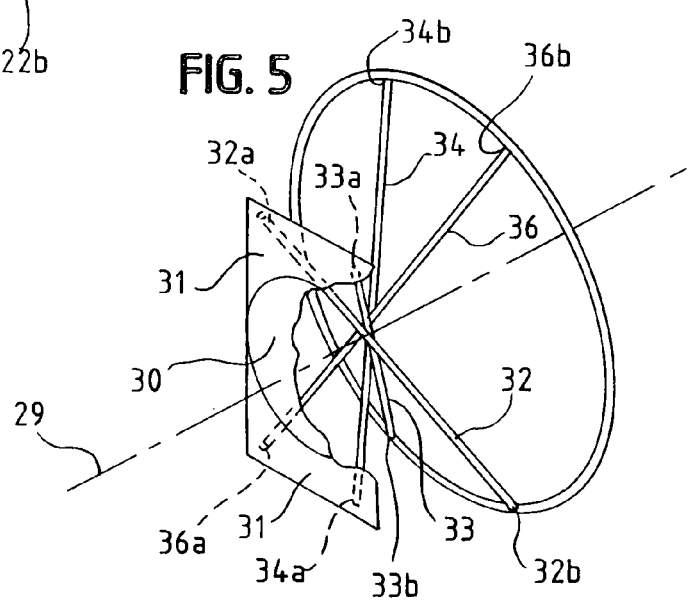
FIG. 5 is a perspective view of the lens of FIG. 4.

Referring to FIGS. 4 and 5 we show an alternative structure for our IOL. The IOL in FIGS. 4 and 5 have a positive lens 30 with a frame 31 integrally extending from its upper and lower circumference encompassing more than 90° of the upper portion and more than 90° of the lower portion. A center line passing through the center of the lens 30 and contacting the any two extremities of the frame has a length less than the diameter length of the sulcus or zonule connecting ring 37. Thus like the embodiment of FIGS. 1–3, the lens frame is entirely within the ring. The lens frame has a pair of spaced upper haptics 32 and 33. Haptic 32 has a first end 32a and haptic 33 has a first end 33a. The first ends 32a and 33a are spaced apart and hinged to the upper portion of the frame 31 adjacent the opposite sides 35a and 35b of the frame upper portion and the frame end 35c. The points of connections on the frame of ends 32a and 33a are spaced at least 15° apart when measured by a radius line from the center of the lens 30 to the points of connection of ends 32a and 33a. The second end 32b of haptic 32 and the second end 33b of haptic 33 are connected to the lower portion of the ring 37 on opposite sides of the lens axis 29.

The frame has a pair of spaced lower haptics 34 and 36. Haptic 34 has a first end 34a and haptic 36 has a first end 36a. The first ends 34a and 36a are spaced apart and hinged to the lower portion of the frame 31 adjacent the opposite sides 35d and 35e of the frame lower portion and the frame lower end 35f. These points of connection on the frame for the ends 34a and 36a are spaced at least 15° apart when measured by a radius line from the center of the lens 30 to the points of connection on the frame for ends 34a and 36a. The second end 34b of haptic 34 and the second end 36b of haptic 36 are connected to the lower portion of the ring 37 on opposite sides of the optical axis 29. < >The sulcus or zonule connecting ring 27 is axially spaced from the lens 20 and is sized to be connected to the sulcus or to be placed in the eye capsule and connected to the zonules.

The lens 30 shown is a positive lens but as stated above if it is desired this may be a negative lens. The rectangular frame 31 preferably has a convex shape.

Figure 6:
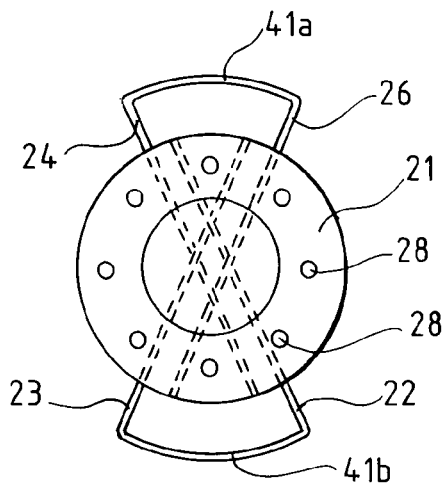
FIG. 6 is a rear plane view of another intraocular lens according to the present invention.

Referring to FIG. 6, the IOL therein has the same general structure of the IOL of FIG. 1 and therefore we have used the same numerals to depict the same items. The only difference between the two structures is that the sulcus or zonule connecting member has a different shape. The connecting member 27 is a ring and the connecting member for FIG. 6 are two arcs 41a and 41b. Haptic ends 24b, 26b are connected to the opposite ends of the arc 41a. Haptic ends 22b, 23b are connected to the opposite ends of the arc 41b.

Figure 7:
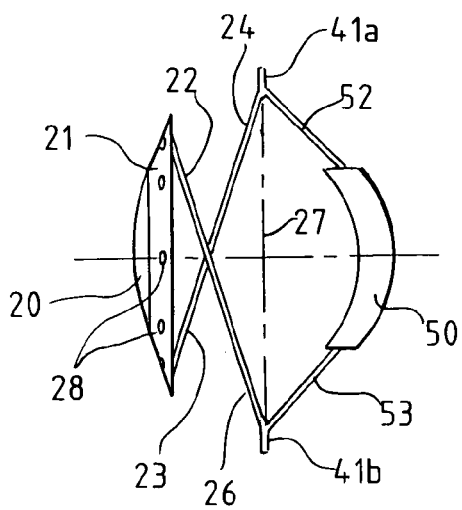
FIG. 7 is a perspective view of another intraocular lens according to the present invention.

Referring to FIG. 7, there is shown another alternative IOL. The IOL in these Figs. have a positive lens 40 with an upper frame 42 and lower frame 43 integrally extending from its upper and lower circumference encompassing more than 90° of the upper portion of lens 40 and more than 90° of the lower portion of lens 40. The upper end 42a of the upper frame 42 forms a cylindrical opening and lower end 43a of the lower frame 43 forms a cylindrical opening. A curved haptic 44 has one end 44b passing through the upper frame opening so that the haptic end freely rotates or pivots in the opening. The elongated haptic end 44b contacts more than one inner surface point of the frame opening 42a to provide stability and even movement of the lens 40 along the optical axis. The other end 44a of the haptic 44 has a curved surface such that the end 44a curves below the lower frame end 43a. and its radius conforms to curvature of the lower sulcus. A second curved haptic 46 has one end 46b passing through the lower frame opening so that the haptic end 46b freely rotates or pivots in the opening. The elongated haptic end 46bcontacts more than one inner surface point of the frame opening 43a to provide stability and even movement of the lens 40 along the optical axis. The other end 46a of the haptic 46 has a curved surface that curves above the upper frame end 42a. and its radius conforms to curvature of the upper sulcus. Thus when the IOL of FIG. 7 is inserted in the eye, it is inserted with the haptic ends contacting the sulcus of the eye so that when the sulcus contracts the lens 40 moves in the direction of the arrow in FIG. 7. When the sulcus relaxes, the lens moves in the opposite direction of the arrow. Alternatively, when this IOL is placed in the eye capsule, it is inserted so that the haptic ends are connected to the inner walls of the capsule so that when the sulcus muscle contracts, the zonules become lax and the lens 40 moves in the direction of the arrow in FIG. 7.

The haptic ends 43a and 44a can if desired be maintained in their respective cylindrical openings by appropriate means to prevent them from exiting the cylinder i.e. appropriate washers. The haptics may have a helical configuration or partial helical configuration as long as one end is above the lens and the other end is below the lens or vice versa and as long as the haptic end connected to the frame has more than one i.e. at least two, contact point with the frame.

FIG. 8 shows one possible configuration of a way in which a positive lens 20 may be coupled mechanically to a negative lens 50, where both lenses comprise an assembled accommodating dual IOL 51. The positive lens IOL is the same as that illustrated in FIGS. 1–3. Of course the other positive lens IOLs note in FIGS. 4–7 may be used instead. The negative lens 50 is connected to the ring 27 by haptics 52 and 53. The haptics 22, 23, 24, 26, 52, and 53 are sized to provide adequate leverage to cause the positive lens 20 and the negative lens 50 to separate when the ciliary muscle contracts. The haptics are generally made of the same polymer material as their respective lens and are preferably integral with their respective lenses. They, of course, may be made of separate materials and appropriately affixed to their respective lenses. The linkages are sufficiently rigid such that a force directed towards the center of the eye by a contracting ciliary muscle causes the lenses 20 and 50 to separate from each other as shown in FIGS. 9 and 10. Each linkage 52 and 53 is semi-rigid straight (or reasonably straight) and has flexure joints (one at the apex of the haptics 52 and 53, and one each linking arm is attached to the lens 50. The configuration shown in FIG. 8 will cause the lenses to separate when a compressive force is applied to the ring 27.

Although the joining of the linkages is preferred, the negative lens haptics 52 and 53 may be separate and not attached. However, they will extend at an angle to the optical axis so that at least the positive lens can move along the optical axis.

Although the hinge configuration in FIG. 8 shows that the haptics have approximately the same length, haptics having different lengths and different angles from those shown in FIG. 8. Another hinge configuration for the negative lens may be used to move the two lenses during accommodation such as a more general "lambda" shape (i.e. the Greek letter λ) or, perhaps, a mirror-image λ shape. Within the practice of mechanical engineering and design, it is obvious to those skill in those fields that there are many other hinge configurations that will result in constraining the movements of the two lenses appropriately in order to achieve the benefits of our invention.

Although FIG. 8 shows the positive and negative lens components of the IOL coupled by mechanical linking arms, two independent (i.e. not linked) lenses conceivably can be implanted in sequence by skilled surgeons at precise locations in either the capsular bag or the ciliary sulcus to achieve good focusing during accommodation.

FIG. 9 (left) shows an accommodating dual IOL 51, which is a mechanically linked positive-negative lens pair, implanted in the ciliary sulcus 62 behind the eye's cornea 63 and in front of the lens capsule 64 with the ciliary muscle 65 relaxed (eye focused at distant object). The dual IOL 51 is mechanically linked after or before being implanted. In this instance lens separation 66 is relatively small. The zonules 67 support the lens capsule 61 from which the cataract has been removed.

FIG. 9 (right) shows the same accommodating dual IOL 51 and how the lens separation 68 increases during accommodation when the ciliary muscle tightens causing the sulcus 62 to constrict. Also shown is how the lens capsule 64 and the supporting zonules 67 tend to move to the right during ciliary muscle contraction.

FIG. 10 (left) shows an accommodating dual IOL 51, which is a mechanically linked positive-negative lens pair, implanted in the lens capsule 64 behind the eye's cornea 63 with the ciliary muscle 65 relaxed (eye focused at distant object). IOL 51 is mechanically linked after or before implantation. In this instance, lens separation 69 is relatively small, since the zonules 67 which are taught exert an outward tension at the edges of the lens capsule 64 where the dual IOL's flexible hinged apex is attached.

FIG. 10 (right) shows the same accommodating IOL 51 implanted in the lens capsule 64 behind the eye's cornea 63, and how the lens separation 70 increases during accommodation when the ciliary muscle 65 tightens causing lax zonules 67 which exert reduced tension at the edges of lens capsule 31 where the IOL's flexible hinged apex is attached.

Our co-pending U.S. Application illustrates ray traces from a computerized lens design program (ZEMAX) which illustrate the movement required from different types of accommodating IOL models for a prescribed amount of accommodation. That and the calculations set forth therein are incorporated in this application by reference.

Various features of the invention have been particularly shown and described in connection with the illustrated embodiment of the invention, however, it must be understood that these particular arrangements merely illustrate, and that the invention is to be given its fullest interpretation within the terms of the appended claims.

The invention claimed is:

1. An eye intraocular lens comprising:
   a lens, said lens having any of the following types of surface shapes: spherical, astigmatic toric, aspherical with or without axial symmetry, multi-zoned surfaces as those found on Fresnel lenses, diffractive surfaces, and one surface diffractive and the other surface diffractive,
   a frame extending from the lens to provide diametrically opposed upper and lower frame sections,
   a first lens linkage having a pair of upper haptics with upper haptic first ends spaced at least 15° apart attached to the upper frame section,
   a second lens linkage having a pair of lower haptics with lower haptic first ends spaced at least 15° apart attached to the lower frame section,
   a second end of said first lens linkage and a second end of the second lens linkage attached to a sulcus or zonule member to provide relatively large movement of the lens with a small movement of the ciliary muscle during accommodation response of the eye,
   said sulcus or zonule member is a connecting ring sized to be attached to an eye's ciliary sulcus or to the interior of an eye's lens capsule,
   said upper pair of haptics has their second ends diametrically connected of a lower section of the ring,
   said lower pair of haptics has their second ends diametrically connected of an upper section of the ring, and
   the intraocular lens is sized to be located within or outside of eye's lens capsule,
   wherein said movements during the accommodation response are along the optical axis of the eye and are controlled in order to improve the image on the retina of objects viewed by the eye over a wide range of distances.

2. The eye intraocular lens of claim 1, wherein the lens is a positive lens and the frame is an open conical shape.

* * * * *